US010329375B2

(12) United States Patent
Stache et al.

(10) Patent No.: US 10,329,375 B2
(45) Date of Patent: Jun. 25, 2019

(54) HYDROPHILIC, ALKOXYSILANE-CONTAINING ISOCYANURATES

(71) Applicant: Evonik Degussa GmbH, Essen (DE)

(72) Inventors: Wiebke Stache, Herten (DE); Tobias Unkelhäußer, Dülmen (DE); Iris Brückner, Dorsten (DE); Sabine Naumann, Herne (DE); Marita Drüner, Reken (DE); Judith Schoder, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/984,139

(22) Filed: May 18, 2018

(65) Prior Publication Data

US 2018/0334532 A1 Nov. 22, 2018

(30) Foreign Application Priority Data

May 19, 2017 (EP) .................................... 17172009

(51) Int. Cl.
| | | |
|---|---|---|
| *C08G 18/83* | (2006.01) | |
| *C07F 7/18* | (2006.01) | |
| *C09D 175/04* | (2006.01) | |
| *C08G 18/73* | (2006.01) | |
| *C08G 18/77* | (2006.01) | |
| *C08G 18/18* | (2006.01) | |
| *C08G 18/28* | (2006.01) | |
| *C09D 175/08* | (2006.01) | |
| *C08G 18/79* | (2006.01) | |
| *C08G 18/80* | (2006.01) | |

(52) U.S. Cl.
CPC .............. *C08G 18/837* (2013.01); *C07F 7/18* (2013.01); *C07F 7/1804* (2013.01); *C07F 7/1892* (2013.01); *C08G 18/1875* (2013.01); *C08G 18/283* (2013.01); *C08G 18/73* (2013.01); *C08G 18/778* (2013.01); *C08G 18/792* (2013.01); *C08G 18/809* (2013.01); *C09D 175/04* (2013.01); *C09D 175/08* (2013.01)

(58) Field of Classification Search
CPC .. C08G 18/837; C08G 18/809; C08G 18/792; C08G 18/283; C08G 18/1875; C08G 18/778; C08G 18/73; C07F 7/18; C07F 7/1804; C07F 7/1892; C09D 175/04
See application file for complete search history.

(56) References Cited

U.S. PATENT DOCUMENTS

| | | | |
|---|---|---|---|
| 4,663,377 | A | 5/1987 | Hombach et al. |
| 5,200,489 | A | 4/1993 | Jacobs et al. |
| 5,252,696 | A | 10/1993 | Laas et al. |
| 5,679,147 | A | 10/1997 | Standke et al. |
| 6,426,414 | B1 | 7/2002 | Laas et al. |
| 2007/0004894 | A1 | 1/2007 | Mazanek et al. |
| 2013/0041102 | A1 | 2/2013 | Albrecht et al. |
| 2014/0037851 | A1 | 2/2014 | Groenewolt et al. |

FOREIGN PATENT DOCUMENTS

| | | |
|---|---|---|
| CN | 105 542 700 | 5/2016 |
| DE | 10 2005 030 523 | 1/2007 |
| EP | 0 206 059 | 12/1986 |
| EP | 0 540 985 | 5/1993 |
| EP | 0 716 128 | 6/1996 |
| EP | 0 959 087 | 11/1999 |
| JP | 2012-183668 | 9/2012 |
| WO | 2011/144644 | 11/2011 |
| WO | 2012/098014 | 7/2012 |

*Primary Examiner* — Christopher M Rodd

(74) *Attorney, Agent, or Firm* — Grüneberg & Myers PLLC

(57) ABSTRACT

A coating or plastics formulation contains a reaction product of at least one alkoxysilane-containing isocyanurate of the formula (I)

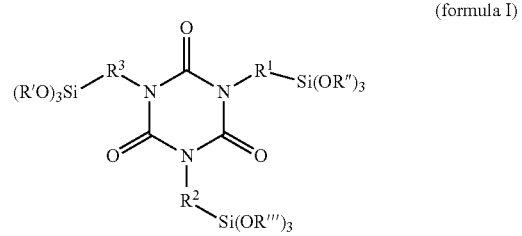

(formula I)

with at least one hydrophilizing agent of the formula BOH which has at least one OH group, wherein $R^1$, $R^2$ and $R^3$ in each case independently of one another are a linear or branched and/or cyclic C1-C8 alkylene radical, R', R" and R'" in each case independently of one another are a linear or branched and/or cyclic C1-C8 alkyl radical, and B is a hydrophilic radical.

10 Claims, No Drawings

HYDROPHILIC, ALKOXYSILANE-CONTAINING ISOCYANURATES

BACKGROUND OF THE INVENTION

Field of the Invention

The present invention relates to innovative, water-dispersible, hydrophilic, alkoxysilane-containing isocyanurates whose possible uses include utility as crosslinkers. The present invention further relates to a process for preparing them, to compositions comprising them and to the use thereof in coating compositions, more particularly as a starting component in the production of polyurethane plastics, as crosslinkers for water-soluble or water-dispersible paint, adhesive or sealant binders, or as a binder component.

Discussion of the Background

For water-soluble or water-dispersible binders there are numerous fields of application, for example in paints, inks, textile treatment products and adhesives. A disadvantage, however, is the weak resistance towards water and chemicals. In this respect, the solvent-containing binders often score better than their aqueous counterparts. In order to strengthen the resistance of water-soluble or water-dispersible binders, a crosslinker is added to the binder. Crosslinkers employed, depending on the binder, include hydrophilic products having methylol, ethyleneimine, epoxy, isocyanate or carbodiimide function.

Water-dispersible polyisocyanates constitute a class of hydrophilic crosslinkers which have gained in importance in recent years for various fields of application. They are nowadays used in particular as crosslinker components for acrylate-based coating materials, high-quality water-thinnable two-component polyurethane coating materials (two-component PU coating materials), or as admixtures for aqueous dispersion-based adhesives. They serve for crosslinking of aqueous dispersions in the finishing of textiles or leather, or for crosslinking formaldehyde-free textile printing inks, and are also suitable, furthermore, for example as auxiliaries for the wet-strengthening of paper, as disclosed in EP 0 959 087 A1, for example.

In practice, employed nowadays for the very great majority of the applications, exclusively, are nonionic polyisocyanates modified hydrophilically by means of polyethers. The preparation of water-dispersible polyisocyanates of these kinds is discussed exhaustively in EP 959 087 A1, EP 206 059 B1 and EP 540 985 A1, for example. The polyisocyanates generally comprise one or more isocyanurate structures.

Additionally, DE 10 2005 030 523 A1 discloses the possibility of using cationic, anionic and/or nonionic compounds, such as mono- and/or dihydroxycarboxylic acids or monofunctional alkyl ethoxylates, including in mixtures with one another, as hydrophilizing agents for polyurethanes. DE 10 2005 030 523 A1 further teaches the use of hydroxy-functional amides of at least difunctional carboxylic acids for the purpose of hydrophilizing polyisocyanates and polyurethanes. The polyurethanes employed there may typically be di- or triisocyanates and also their higher molecular mass derivatives having urethane, allophanate, biuret, uretdione and/or isocyanurate groups, with two or more free NCO groups.

Against the background of increasingly stringent environmental legislation, a search is on for toxicologically unobjectionable, NCO-free alternatives to the hydrophilic polyisocyanates, which as far as possible fulfil the same requirements.

Alkoxysilane-based systems constitute in principle one less toxicologically objectionable alternative to the existing hydrophilic crosslinkers with methylol, ethyleneimine, epoxy or isocyanate function. Some alkoxysilane-based systems, such as aminoalkylalkoxysilanes, for example, are even water-soluble, Additionally, water-based compositions with polyfunctional organopolysiloxanes which possess silanol groups are known for use as adhesion promoters; cf. EP 0 716 128 A2. The silanols are of only limited suitability as crosslinkers for aqueous binder components, since either they are too reactive or they do not fulfil the same requirements as hydrophilic polyisocyanates in relation to the coatings properties.

SUMMARY OF THE INVENTION

It is an object of the present invention, therefore, to provide compositions which avoid the aforesaid disadvantages, and more particularly to provide alkoxysilane-containing, water-dispersible crosslinkers which can be homogenized well in aqueous binder compositions and which allow a long working time. This and other objects have been achieved by the present invention, the first embodiment of which includes a reaction product, in accordance with the invention, of an alkoxysilane-containing isocyanurate of the formula (I)

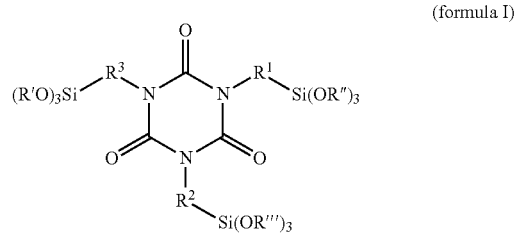

(formula I)

with at least one hydrophilizing agent of the formula BOH which has at least one OH group, wherein $R^1$, $R^2$ and $R^3$ in each case independently of one another are a linear or branched and/or cyclic C1-C8 alkylene radical, R', R" and R'" in each case independently of one another are a linear or branched and/or cyclic C1-C8 alkyl radical and B is a hydrophilic radical.

Surprisingly, these hydrophilized isocyanurates, especially as compared with physical mixtures of hydrophilizing agents, display effective dispersibility.

DETAILED DESCRIPTION OF THE INVENTION

Any ranges mentioned herein below include all values and subvalues between the lowest and highest limit of this range.

One embodiment relates to a reaction product of an alkoxysilane-containing isocyanurate of the formula (I)

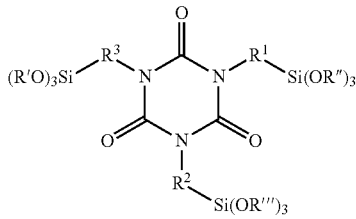

(formula I)

with at least one hydrophilizing agent of the formula BOH which has at least one OH group,
wherein
$R^1$, $R^2$ and $R^3$ in each case independently of one another are a linear or branched and/or cyclic C1-C8 alkylene radical,
R', R" and R'" in each case independently of one another are a linear or branched and/or cyclic C1-C8 alkyl radical and
B is a hydrophilic radical.

$R^1$, $R^2$, $R^3$, R', R" and R'" may each be present linearly, branched, in cyclic form or in structures with linear and/or branched structures with cyclic fractions.

In the reaction of the at least one isocyanurate of the formula (I) with at least one hydrophilizing agent BOH there is a transesterification in which a radical —OB is introduced onto an alkoxysilane group with elimination of HOR'.

In the case of a 1:1 reaction (based on isocyanurate and hydrophilizing agent) or in the case of a 9:1 reaction (based on the alkoxy groups present and radicals —OH of the hydrophilizing agent), respectively, therefore, a trialkoxysilyl radical —Si(OR')$_3$ is converted into a radical —Si(OR')$_2$OB.

In principle only one trialkoxysilyl group of the isocyanurate may have been singly transesterified. It is also possible, however, for one trialkoxysilyl group of the isocyanurate to have been transesterified twice or even three times, or for two or all three alkoxysilyl groups of the isocyanurate to have been transesterified singly, twice or even three times.

Moreover, in the reaction of the alkoxysilane-containing isocyanurate of the formula (I) with the hydrophilizing agent B, it is also possible for two or more isocyanurates to react with one another in the presence of traces of water, by formal elimination of $R'^{/"/'''}OR'^{/"/'''}$, with crosslinking, in a condensation reaction to form siloxane structures. It is likewise conceivable that where hydrophilizing agents are used that have two or more radicals —OH, two isocyanurates will react with the same hydrophilizing agent and therefore also form compounds of relatively high molecular mass. For this reason, it not possible to state a unitary structural formula for the reaction of the at least one isocyanurate with the at least one hydrophilizing agent.

The hydrophilized, alkoxysilane-containing compound is preferably the reaction product of exactly one single isocyanurate with one or more hydrophilizing agents BOH.

Such compounds have the formula (II)

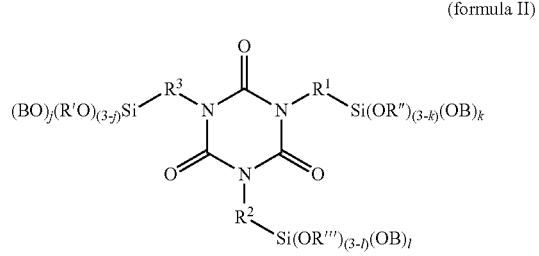

(formula II)

wherein
$R^1$, $R^2$ and $R^3$ in each case independently of one another are a linear or branched and/or cyclic C1-C8 alkylene radical,
R', R" and R'" in each case independently of one another are a linear or branched and/or cyclic C1-C8 alkyl radical,
j, k, l each independently of one another are 0, 1, 2 or 3, $1 \leq j+k+l \leq 7$ and
B is a hydrophilic radical.

Corresponding compounds also have the advantage that they endow coating materials in which they are used, for example, as crosslinkers with particularly good chemical stability. Hence it is possible without problems to obtain chemical resistances of at least 100 MEK double rubs.

Although in principle the radicals $R^1$, $R^2$ and $R^3$ may each independently of one another be linear or branched and/or cyclic C1-C8 alkylene radicals, it is preferred for $R^1$, $R^2$ and $R^3$ to be identical, i.e. $R^1=R^2=R^3$. It is also possible in principle for each R', R" and R'" to be a different linear or branched and/or cyclic C1-C8 alkyl radical. Preferably, however, all of radicals R', R" and R'" are identical. $R^1$, $R^2$, $R^3$ and R', R" and R'" may in each case be linear, branched, cyclic or present in structures having linear and/or branched structures with cyclic fractions.

Preferred alkoxysilane-containing isocyanurates of the formula (I) are
1,3,5-tris[3-(trimethoxysily)methyl]-1,3,5-triazine-2,4,6 (1H,3H,5H)-trione,
1,3,5-tris[3-(triethoxysily)methyl]-1,3,5-triazine-2,4,6(1H,3H,5H)-trione,
1,3,5-tris[3-(tri-iso-propoxysilyl)methyl]-1,3,5-triazine-2,4,6(1H,3H,5H)-trione,
1,3,5-tris[3-(trimethoxysily)ethyl]-1,3,5-triazine-2,4,6(1H,3H,5H)-trione,
1,3,5-tris[3-(triethoxysily)ethyl]-1,3,5-triazine-2,4,6(1H,3H,5H)-trione,
1,3,5-tris[3-(tri-iso-propoxysily)ethyl]-1,3,5-triazine-2,4,6 (1H,3H,5H)-trione,
1,3,5-tris[3-(trimethoxysilyl)propyl]-1,3,5-triazine-2,4,6 (1H,3H,5H)-trione,
1,3,5-tris[3-(triethoxysilyl)propyl]-1,3,5-triazine-2,4,6(1H,3H,5H)-trione,
1,3,5-tris[3-(tri-iso-propoxysilyl)propyl]-1,3,5-triazine-2,4,6(1H,3H,5H)-trione,
1,3,5-tris[3-(trimethoxysilyl)butyl]-1,3,5-triazine-2,4,6(1H,3H,5H)-trione,
1,3,5-tris[3-(triethoxysilyl)butyl]-1,3,5-triazine-2,4,6(1H,3H,5H)-trione,
1,3,5-tris[3-(tri-iso-propoxysilyl)butyl]-1,3,5-triazine-2,4,6 (1H,3H, ,5H)-trione, and mixtures thereof.

R', R" and R'" are therefore preferably identical and selected from the group consisting of —CH$_3$, —CH$_2$CH$_3$, —CH(CH$_3$)CH$_3$ and R$^1$=R$^2$=R$^3$=—CH$_2$—, —CH$_2$CH$_2$—, —CH$_2$CH$_2$CH$_2$—, —CH$_2$CH$_2$CH$_2$CH$_2$—.

Particularly preferred compounds of the formula (I) are 1,3,5-tris[3-(triethoxysilyl)propyl]-1,3,5-triazine-2,4,6(1H,3H,5H)-trione, and 1,3,5-tris[3-(trimethoxysilyl)propyl]-1,3,5-triazine-2,4,6(1H,3K5H)-trione. Especially preferred is 1,3,5-tris[3-(trimethoxysilyl)propyl]-1,3,5-triazine-2,4,6(1H,3H,5H)-trione. Accordingly, the compound of the formula (II) derives very preferably from these compounds of the formula (I). It is preferred, therefore, if R$^1$=R$^2$=R$^3$=—CH$_2$CH$_2$CH$_2$— and R'=R"=R'" selected from the group consisting of —CH$_3$, —CH$_2$CH$_3$.

Suitable hydrophilizing agents of the formula BOH may be ionic (cationic or anionic) or nonionic hydrophilizing agents. Nonionic hydrophilizing agents are preferred. The hydrophilizing agent of the formula BOH is further characterized in that it carries at least one OH group. Use may be made in particular of mono- and/or dihydroxycarboxylic acids, hydroxysulfonic acids, mono- or dihydroxy-functional carboxamides and monohydroxy-functional alkyl ethoxylates. The hydrophilizing agent preferably has precisely one OH group. Preferably, therefore, the radical B is a radical derived from a mono- or dihydroxycarboxylic acid, from a mono- or dihydroxy-functional carboxamide or from a monohydroxy-functional alkyl ethoxylate.

Preferred examples of suitable nonionic hydrophilizing agents BOH are polyalkylene oxide polyether alcohols, of the kind obtainable conventionally by alkoxylation of suitable starter molecules. Preferably, therefore, the radical —OB of the hydrophilizing agent is a polyalkylene oxide polyether alkyl radical. The polyalkylene oxide polyether alcohols may be prepared using any desired monohydric alcohols of the molecular weight range from 32 to 150, of the kind also used according to EP 206 059 B1, for example, as starter molecules. A particularly preferred starter molecule used is methanol. Alkylene oxides suitable with preference for the alkoxylation reaction are, in particular, ethylene oxide and propylene oxide, which may be used in any order or else in a mixture in the alkoxylation reaction. Preferred polyalkylene oxide polyether alcohols are either pure polyethylene oxide polyether alcohols or mixed polyalkylene oxide polyether alcohols in which at least 70 mol %, preferably at least 80 mol %, of the alkylene oxide units consist of ethylene oxide units. Particularly preferred polyalkylene oxide polyether alcohols are pure polyethylene glycol monomethyl ether alcohols which have on average 5 to 30, more preferably 6 to 15, ethylene oxide units. Preferred radicals —OB are therefore polyethylene glycol monomethyl ether alkoxy radicals having on average 5 to 30, more preferably 6 to 15, ethylene oxide units.

Examples of corresponding commercially available polyalkylene oxide polyether alcohols that can be used are the Polyglykols M350, M350 PU (lower water content than M350), M500, M500 PU, M750 and M1000 from Clariant (linear, monohydroxy-functional polyethylene glycol monomethyl ethers having respective molar masses of approximately 350 g/mol, 500 g/mol, 750 g/mol and 1000 g/mol). Preference is given to using linear, monohydroxy-functional polyethylene glycol monomethyl ethers having molar masses of approximately 350 g/mol to 500 g/mol.

Likewise, preferred radicals —OB derive from compounds which are similar to the hydrophilizing agents described in WO 2011/144644 A1. Preferred hydrophilizing agents, accordingly, are compounds BOH where B=(X)-(y)$_a$-(Z). Preferred radicals —OB therefore have the formula —O{(X)-(y)$_a$-(Z)}.

In this formula, X is one or more hydrophilic structural units, y is an optional spacer, a is 0 or 1, and Z is one or more hydrophobic structural units.

The hydrophilizing agent may be formed by reaction of X', optionally y' and Z'.

X', y' and Z' contain functional groups which are complementary to one another, so that reaction of these functional groups leads to covalent bonds and hence to the hydrophilizing agent of the formula HO{(X)-(y)$_a$-(Z)}. The hydrophilizing agent in this case contains at least one or more OH groups. In one preferred embodiment this OH group lies approximately or exactly between X and Z. These OH groups may already have been present in X', y' or Z'. Preferably, however, this OH group arises from reaction of X', optionally y' and Z'. The hydrophilic structural constituent X originates from the compound class X'. X' possesses at least one functional group which is able to react with y' or Z', and X', optionally after neutralization of ionogenic (neutralizable) groups possibly present, is inherently water-soluble or water-dispersible, i.e. hydrophilic, in accordance with the above-described definition of "water-soluble" and "water-dispersible".

Preferably X' is a) a hydroxypolyether containing predominantly polyethylene glycol units, with pure hydroxypolyethylene glycol ethers conforming to the empirical formula HO(CH$_2$CH$_2$O)$_n$T$^1$ where n=2-100, preferably n=2-50, wherein T$^1$ is either H or an alkyl group having 1-6 carbon atoms; and/or b) one or more compounds having ionogenic groups, more particularly carboxylic acid groups or sulfonic acid groups. Carboxylic acids contemplated include, preferably, hydroxyalkylcarboxylic acids, more particularly dimethylolpropionic acid, hydroxyacetic acid, hydroxypropionic acid or hydroxybutyric acid. Sulfonic acids contemplated comprise, preferably, hydroxyalkylsulfonic acids or hydroxypolyethersulfonic acids.

Neutralizing agents contemplated for the ionogenic groups b) containing acid groups are preferably alkali metal or alkaline earth metal hydroxides.

Both a) and b) have at least one, or two or more, OH group(s). Preference is given to exactly one OH group.

Combinations of a) and b) are also possible.

Employed with preference as X' component a) are alkanol-started polyalkylene oxide monoalcohols. These compounds are also available commercially, in the form, for example, of Polyglykol M 250, M 350, M350 PU, M 500, M 500 PU, M 750 and M 1 100 from Clariant, For preparing the alkanol-started polyalkylene oxide monoalcohol X' from an initial alcohol having 1-6 carbon atoms, the first step is to add on ethylene oxide and/or propylene oxide to this alcohol. Where both alkylene oxides are used, the addition may take place randomly, blockwise and as a gradient.

In the case of the random addition, a mixture of the desired proportions of ethylene oxide and propylene oxide is added onto the starting alcohol. In the case of the blockwise addition, the components are each added on in stages separate from one another. In the case of the gradient addition, both alkylene oxides are metered in simultaneously or with variable relative metering rate.

Preferably X' consists exclusively of polyethylene glycol units (variant a) and is described by the formula HO(CH$_2$CH$_2$O)$_n$T$^1$, where T$^1$=—(CH$_2$)$_m$CH$_3$. More preferably, m=0-3. Here, n=2-100, preferably n=2-50 and more preferably n=2-25. This preferred component X for preparing the emulsifier B) is an alkanol-started polyethylene oxide monoalcohol.

The optional component y' is an at least difunctional spacer which is capable of reacting both with X' and with Z'. It may preferably be a di- or polyisocyanate, di- or polycarboxylic acid derivative, di- or polyepoxide, or a mono- or polyalkoxysilane. Mixed functionalities are conceivable as well, especially an epoxyisocyanate, an epoxyalkoxysilane, an isocyanatosilane.

The hydrophobic structural constituent Z originates from the class of compound. Z' possesses at least one functional group which is able to react with y' or X', and Z' per se is insoluble in water, i.e. hydrophobic. Preferably Z' is
a) a hydroxy-terminated polyether which comprises or consists of one or more different polyglycol units $TO(CTHCH_2O)_n(CH_2CH_2O)_pT'$, preferably consisting thereof, wherein T is a hydrocarbon radical of the formula $-(CH_3)_mCH_3$, n and m independently of one another=0-20 and p=0-5, where n is greater than or equal to 4 times p, and T' independently at each occurrence is either H or alkyl having 1-18 carbon atoms; and/or
b) one or more hydroxyhydrocarbons having 1-18 carbon atoms, which may also be branched and/or contain rings and/or heteratoms, more particularly hexanol, octanol, decanol, and/or dodecanol and further homologues, and/or
c) an alkylene oxide, which may also be branched and/or contain rings, this oxide having at least four carbon atoms. Suitability here is possessed in particular by butylene oxide, pentene epoxide, hexene epoxide, heptene epoxide, octene epoxide, nonene epoxide, decene epoxide, undecene epoxide, and/or dodecene epoxide and further homologues.

Preferred as Z' are alkylene oxides c) (epoxides) having 8-14 carbon atoms.

Each of a), b) and c) has at least one, or two or more, OH group(s) or other group(s) reactive towards X' or y'. The variant c) is preferred.

Combinations of a), b) and c) are also possible.

An essential feature of Z' is that per se it is not water-soluble or water-dispersible. Preferably Z' comprises a hydrocarbon having at least eight carbon atoms and at least one epoxide group.

The radicals X, y and Z in the stated preferred radical $—O\{(X)-(y)_a-(Z)\}$ are therefore derived, correspondingly, from the compounds X', optionally y' and Z', used for generating the hydrophilizing agent.

Preferred, furthermore, is an isocyanurate having at least one radical $—O\{(X)-(y)_a-(Z)\}$ wherein the radical X derives
from a hydroxypolyethylene glycol ether of the empirical formula $HO(CH_2CH_2O)_nT^1$ where n=2-100, where $T^1$=H or $C_1$-$C_6$ alkyl,
from a hydroxyalkylcarboxylic acid or
from a hydroxypolyethersulfonic acid;
the radical y, if present, derives from a di- or polyisocyanate, from a di- or polycarboxylic acid derivative, from a di- or polyepoxide, from a mono- or polyalkoxysilane, from an epoxyisocyanate, from an epoxyalkoxysilane or from an isocyanatosilane; and
the radical Z derives
from a hydroxy-terminated polyether of the formula $TO(CTHCH_2O)_n(CH_2CH_2O)_pT'$, wherein $T=-(CH_2)_mCH_3$, n and m independently of one another=0-20, p=0-5 where n is greater than or equal to 4 times p, and $T'$=H or $C_1$-$C_{18}$ alkyl,
from one or more than one hydroxyhydrocarbon having 1-18 carbon atoms, which is optionally branched and/or optionally contains rings and/or heteroatoms, or
from an alkylene oxide having at least four carbon atoms which is optionally branched and/or optionally contains rings.

The hydrophilizing agent preferably contains precisely one OH group.

Described below is one especially preferred embodiment of the hydrophilizing agent, in which X comprises an alkanol-started polyethylene glycol unit and Z comprises a relatively long hydrocarbon radical and an alcohol group.

In this especially preferred embodiment, the hydrophilizing agent corresponds to the formula X-G-D-H (where -G-D-H=Z),
wherein
X derives from an alkanol-started polyalkylene glycol monoalcohol comprising predominantly ethylene oxide units, preferably from a hydroxypolyalkylene glycol ether of the empirical formula $HO(CH_2CH_2O)_nT^1$ where n=2-100, where $T^1$=H or $C_1$-$C_6$ alkyl, and
G is a structural element of the formula (III)

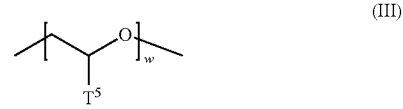

(III)

wherein $T^5$ independently at each occurrence is a saturated, unsaturated, branched or unbranched, substituted or unsubstituted hydrocarbon radical having at least two carbon atoms, preferably 6-12 carbon atoms, and w is greater than or equal to one;
D is an oxyethylene radical or oxypropylene radical of the formula $—(CH_2CHT^6O)_w$ where w is greater than or equal to 0, preferably 0-2, and $T^6$=H or $CH_3$: and
H=hydrogen.

Preferably w is 1-20, more preferably 1-5, very preferably 1-2.

For preparing the alkanol-started polyalkylene glycol monoalcohol from an initial alcohol having 1-6 carbon atoms, the first step is to add on ethylene oxide and/or propylene oxide to this alcohol. Where both alkylene oxides are used, the addition may take place randomly, blockwise and as a gradient. In the case of the random addition, a mixture of the desired proportions of ethylene oxide and propylene oxide is added onto the starting alcohol. In the case of the blockwise addition, the components are each added on in stages separate from one another. In the case of the gradient addition, both alkylene oxides are metered in simultaneously or with variable relative metering rate.

Preferably the polyalkylene glycol monoalcohol consists exclusively of polyethylene glycol units (variant a) and is described by the formula $HO(CH_2CH_2O)_nT^1$ where $T^1=—(CH_2)_mCH_3$. More preferably, m=0-3. Here, n=2-100, preferably n=2-50 and more preferably n=2-25.

This preferred component for preparing the hydrophilizing agent is an alkanol-started polyethylene oxide monoalcohol.

An alkanol-started polyalkylene glycol monoalcohol of this kind (corresponding to X' and also available commercially as, for example, Polyglykol M 250, M 350, M350 PU, M 500, M 500 PU, M 750, M 1 100 from Clariant) is introduced and, under suitable conditions known to the skilled person, is reacted with one or more epoxides with a relatively long alkyl chain having at least three carbon units, preferably at least four carbon units. When ring opening has taken place, the resultant secondary alcohol may optionally be reacted further with ethylene oxide or propylene oxide under the same conditions. This produces a molecule having a hydrophilic unit, with the radical of the alkanol-started polyalkylene glycol monoalcohol from X', intrinsically water-soluble, and a hydrophobic unit, with the radical of the epoxide with a relatively long alkyl chain Y', intrinsically water-insoluble, and during the linking of the two units an alcohol group is formed which is needed for attachment to the alkoxysilane-containing isocyanurate.

In this way, the hydrophilizing agents of the especially preferred embodiment are obtained.

A further subject of the present invention is also a process for preparing a hydrophilically modified alkoxysilane-containing isocyanurate of the invention, wherein at least one alkoxysilane-containing isocyanurate of the formula (I)

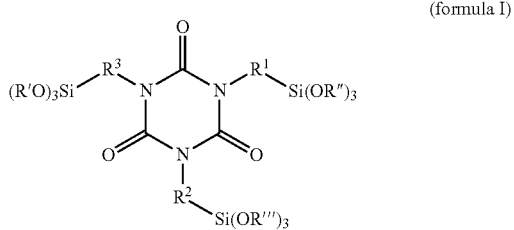

(formula I)

is reacted with at least one hydrophilizing agent of the formula BOH which has at least one OH group, wherein $R^1$, $R^2$ and $R^3$ in each case independently of one another are a linear, branched or cyclic C1-C8 alkyene radical, R', R" and R''' in each case independently of one another are a linear, branched or cyclic C1-C8 alkyl radical, and B is a hydrophilic radical.

The reaction may in principle take place in the presence of solvent, or solventlessly. The process is preferably carried out solventlessly. Furthermore, the reaction may take place batchwise or continuously. The reaction can be carried out in suitable assemblies, especially in stirred tanks, extruders, static mixers and kneading chambers, in each case with a distillation bridge for distillative removal of the liberated alcohol. The removal of the liberated alcohol may with preference be made easier through reduced pressure, through an enlargement in the surface area, or by the passing of an inert gas stream through the reaction mixture. The reaction is carried out at temperatures in the range from 80° C. to 200° C., more particularly in the range from 120 to 180° C., especially preferably in the range from 140 to 160° C. The reaction is conducted with exclusion of water. The reaction is preferred carried out under nitrogen, and more preferably the nitrogen is flushed continuously from the reaction vessel in the direction of the distillation bridge.

To accelerate the reaction it is possible to use known catalysts C) for the esterification. Typical catalysts are organotitanium or organotin compounds such as tetrabutyl titanate or dibutyltin oxide. Also conceivable are catalysts based on other metals, such as zinc, antimony or manganese, an example being manganese(II) acetylacetonate. Likewise possible is the use of metal-free esterification catalysts.

In addition, it is possible to add further additives and processing auxiliaries such as antioxidants or colour stabilizers.

In accordance with the invention, the alkoxysilane-containing isocyanurate of the formula (I) and the hydrophilizing agent BOH are used in a (I)/BOH molar ratio of from 15:1 to 1:7, preferably from 5:1 to 1:1, particularly preferably of 2.7:1. The catalyst C) is used preferably in amounts of 0.0% to 1.0%, more preferably in amounts of 0.1-0.5%.

Percentages here and below, unless otherwise indicated, relate to weight percentages.

The conversion in the reaction may be monitored gravimetrically on the basis of the quantity of liberated alcohol produced during the transesterification. The conversion in the process of the invention for preparing hydrophilic crosslinker U) of the invention is at least 25%, preferably at least 50%, more preferably at least 85%.

A further subject of the present invention is the use of the compounds of the invention as a constituent of coating or plastics formulations. Coating formulations here and below refer in particular to paint, adhesive and sealant formulations.

With advantage the compounds of the invention in this case can be used as crosslinkers. Another subject of the invention, therefore, is the use of the compounds of the invention as crosslinkers, more particularly in plastics and coating formulations.

It has surprisingly been observed, moreover, that prior to the emulsification it is also possible for further, non-hydrophilized alkoxysilanes, polyisocyanates or other hydrophobic coatings additives to be added to the hydrophilic compounds of the invention. In such mixtures the hydrophilic compounds of the invention may take on the function of an emulsifier for the subsequently admixed fraction of non-hydrophilic crosslinkers, e.g. non-hydrophilized, alkoxysilane-containing isocyanurates. Hence another subject of the present invention is the use of the compounds of the invention as emulsifiers, more particularly in plastics and coating formulations.

A further subject of the invention is coating or plastics formulations comprising at least one compound of the invention. The formulations may preferably further comprise isocyanurates of the formula (I)

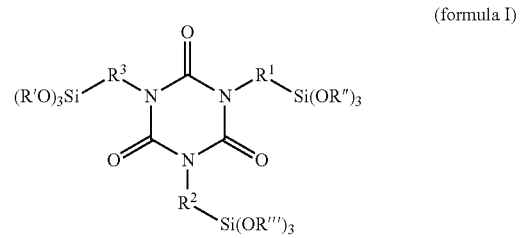

(formula I)

since the compounds of the invention, surprisingly, are especially suitable as emulsifiers for these compounds. With particular preference in this case the molar ratio of the compounds of the invention to the compounds of the formula (I) is 100:1 to 1:14, preferably 10:1 to 1:5.

Another subject of the invention is the use of the compounds of the invention for producing polyurethane plastics, more particularly as crosslinkers for water-soluble or water-dispersible paint binders, adhesive binders or sealant binders, or binder components with or without hydroxyl groups. In particular the compounds of the invention are suitable as crosslinkers for water-soluble or water-dispersible paint binders or paint binder components, especially for two-component PU systems, and also for producing coatings using aqueous coating materials based on such binders or binder components, especially for two-component PU systems.

The compounds of the invention represent valuable starting materials for the production of polyurethane plastics and/or acrylate plastics, since via intermolecular siloxane bonds they are able to form an interpenetrating network or via a transesterification reaction they are able to attach to the OH functions of the plastic, with new Si—O bonds possibly being formed.

For this purpose, the compounds of the invention are used preferably in the form of aqueous dispersions or emulsions, which in combination with water-dispersed polyhydroxyl compounds can be brought to reaction in the form of aqueous two-component (2K) systems.

With particular preference the compounds of the invention are used as crosslinkers for aqueously dissolved or dispersed paint binders or paint binder components having hydroxyl groups, and in the production of coatings using aqueous coating materials based on such binders and/or binder components. The crosslinker, optionally in emulsified form, may be united here with the binders and/or binder components by simply stirring them together prior to the processing of the coating materials by any desired methods, by using mechanical assistants known to the skilled person, or else using two-component spray guns.

In this context, the following paint binders or paint binder components may be mentioned by way of example: Polyacrylates dissolved or dispersed in water and containing hydroxyl groups, more particularly polyacrylates of the molecular weight range 1000 to 10 000, which with the alkoxysilane-functionalized hydrophilic compounds of the invention as crosslinkers constitute valuable two-component binders, or polyester resins in dispersion in water, optionally urethane-modified, and containing hydroxyl groups, these resins being of the kind known from polyester chemistry and alkyd resin chemistry. Suitable in principle as reaction partners for the compounds of the invention are all binders which have OH groups and are present in solution or dispersion in water.

In the case of the inventive use as crosslinker component for aqueous paint binders and in the coating and plastics formulations of the invention, the hydrophilic compounds of the invention are used generally in amounts of 0.5% to 20%, preferably of 2.5 to 15%, more preferably of 8% to 12%.

Non-functional aqueous paint binders as well may be admixed to the hydrophilic compounds of the invention, in minor amounts, in order to obtain very specific properties, for example as an additive to promote adhesion. Of course, the crosslinkers of the invention can also be used with blocked polyisocyanates known per se from polyurethane chemistry, in combination with the abovementioned aqueous paint binders or paint binder components, as aqueous one-component PU baking systems (1K PU).

Substrates contemplated for the aqueous coatings formulated using the compounds of the invention are any desired substrates, such as, for example, metal, wood, glass, stone, ceramic materials, concrete, rigid and flexible plastics, textiles, leather and paper, which may optionally also have been provided with customary primers prior to coating.

Generally speaking, the aqueous coating materials formulated with the compounds of the invention, and optionally admixed, possibly, with the auxiliaries and admixtures customary in the coatings sector, such as flow control assistants, colour pigments, fillers, matting agents or emulsifiers, for example, possess good technical coatings properties even on room-temperature drying. Of course, however, they can also be cured under forced conditions at elevated temperature or by baking at temperatures up to 260° C. On account of their outstanding dispersibility or emulsifiability in water, which allows a homogeneous and particularly fine distribution in aqueous paint binders, the use of the compounds of the invention as a crosslinker component for aqueous polyurethane paints leads to coatings having outstanding optical properties, especially high surface gloss, levelling, and high transparency.

Besides their use as crosslinker components for aqueous two-component PU paints, the compounds of the invention are outstandingly suitable as crosslinkers for aqueous dispersion-based adhesives, leather coatings and textile coatings, or textile printing pastes, as AOX-free paper assistants, or else as admixtures for mineral building materials, examples being concrete or mortar compositions.

Moreover, on the basis of their outstanding dispersibility or emulsifiability in water, the compounds of the invention are also used as adjuvants in aqueous polyurethane dispersions.

The compounds of the invention, processes for preparing them, and their use are described below by way of example, without any intention that the invention should be confined to these exemplary embodiments. When ranges, general formulae or classes of compounds are specified below, these are intended to encompass not only the corresponding ranges or groups of compounds which are explicitly mentioned but also all subranges and subgroups of compounds which can be obtained by leaving out individual values (ranges) or compounds. Where documents are cited for the purposes of the present description, the entire content of these is intended to be part of the disclosure of the present invention.

Embodiments

1. Reaction product of at least one alkoxysilane-containing isocyanurate of the formula (I)

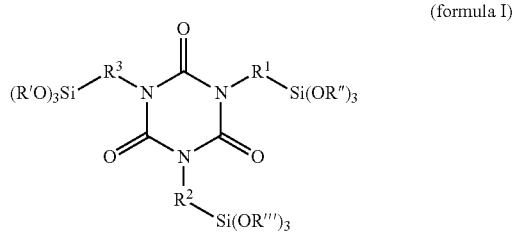

(formula I)

with at least one hydrophilizing agent of the formula BOH which has at least one OH group, wherein $R^1$, $R^2$ and $R^3$ in each case independently of one another are a linear or branched and/or cyclic C1-C8 alkylene radical, R', R" and R''' in each case independently of one another are a linear or branched and/or cyclic C1-C8 alkyl radical and B is a hydrophilic radical.

2. Alkoxysilane-containing isocyanurate of the formula (II)

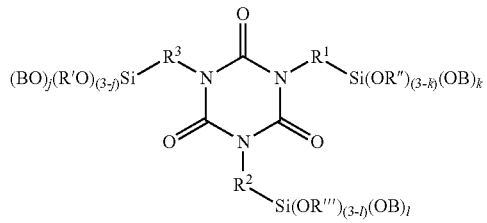

(formula II)

wherein $R^1$, $R^2$ and $R^3$ in each case independently of one another are a linear or branched and/or cyclic C1-C8 alkylene radical, R', R" and R'" in each case independently of one another are a linear or branched and/or cyclic C1-C8 alkyl radical, j, k, l each independently of one another are 0, 1, 2 or 3, $1 \leq j+k+l \leq 7$ and B is a hydrophilic radical.

3. Isocyanurate according to 1 or 2, characterized in that $R^1=R^2=R^3=$ —$CH_2$—, —$CH_2CH_2$—, —$CH_2CH_2CH_2$— or —$CH_2CH_2CH_2CH_2$— and R', R" and R'" are identical and selected from the group consisting of —$CH_3$, —$CH_2CH_3$, —$CH(CH_3)CH_3$.

4. Isocyanurate according to 3, characterized in that $R^1=R^2=R^3=$ —$CH_2CH_2CH_2$— and R', R" and R'" are identical and selected from the group consisting of —$CH_3$, —$CH_2CH_3$.

5. Isocyanurate according to any of 1 to 4, characterized in that the radical —OB of the hydrophilizing agent is a polyalkylene oxide polyether alkoxy radical.

6. Isocyanurate according to 5, characterized in that the polyalkylene oxide polyether alkoxy radical is a polyethylene glycol monomethyl ether alkoxy radical having on average 5 to 30 ethylene oxide units.

7. Isocyanurate according to any of the preceding embodiments, characterized in that the radical —OB has the formula —O{(X)-(y)$_a$-(Z)}, wherein X is one or more hydrophilic structural units, y is an optional spacer, a is 0 or 1, and Z is one or more hydrophobic structural units.

8. Isocyanurate according to 7, characterized in that the radical X derives from a hydroxypolyethylene glycol ether of the empirical formula HO(CH$_2$CHO)$_n$T$^1$ where n=2-100, where T$^1$=H or C$_1$-C$_6$ alkyl, from a hydroxyalkylcarboxylic acid or from a hydroxypolyethersulfonic acid, the radical y, if present, derives from a di- or polyisocyanate, from a di- or polycarboxylic acid derivative, from a di- or polyepoxide, from a mono- or polyalkoxysilane, from an epoxyisocyanate, from an epoxyalkoxysilane or from an isocyanatosilane and the radical Z derives from a hydroxy-terminated polyether of the formula TO(CTHCH$_2$O)$_n$(CH$_2$CH$_2$O)$_p$T', wherein T=—(CH$_2$)$_m$CH$_3$, n and m independently of one another=0-20, p=0-5 where n is greater than or equal to 4 times p, and T'=H or C$_1$-C$_{18}$ alkyl, from one or more than one hydroxyhydrocarbon having 1-18 carbon atoms, which is optionally branched and/or optionally contains rings and/or heteroatom(s), or from an alkylene oxide having at least four carbon atoms which is optionally branched and/or optionally contains rings 9. Isocyanurate according to 7, characterized in that the radical X derives from an alkanol-started polyalkylene glycol monoalcohol comprising predominantly ethylene oxide units and the radical Z has the formula -G-D-H, wherein G is a structural element of the formula (III)

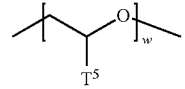

(III)

wherein T$^5$ independently at each occurrence is a saturated, unsaturated, branched or unbranched, substituted or unsubstituted hydrocarbon radical having at least two carbon atoms and w is greater than or equal to one;

D is an oxyethylene radical or oxypropylene radical of the formula —(CH$_2$CHT$^6$O)$_v$ where v is greater than or equal to 0, preferably 0-2, and T$^6$=—H or —CH$_3$; and H=hydrogen.

10. Process for preparing a reaction product and/or an isocyanurate according to any of the preceding claims, characterized in that at least one alkoxysilane-containing isocyanurate of the formula (I)

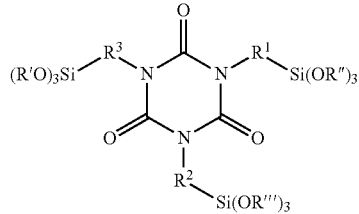

(formula I)

is reacted with at least one hydrophilizing agent of he formula BOH which has at least one OH group, wherein $R^1$, $R^2$ and $R^3$ in each case independently of one another are a linear, branched or cyclic C1-C8 alkylene radical, R', R" and R'" in each case independently of one another are a linear, branched or cyclic C1-C8 alkyl radical, and B is a hydrophilic radical.

11. Process according to 10, characterized in that the alkoxysilane-containing isocyanurate of the formula (I) and the hydrophilizing agent BOH are used in a (I)/BOH molar ratio of preferably from 15:1 to 1:7.

12. Use of a reaction product and/or of an isocyanurate according to any of embodiments 1-9 as constituent of coating or plastics formulations, as crosslinker, as emulsifier, as admixture for mineral building materials and/or as adjuvant for aqueous polyurethane dispersions.

13. Coating or plastics formulation comprising at least one reaction product and/or isocyanurate according to any of embodiments 1-9.

14. Coating or plastics formulation according to 13, further comprising at least one isocyanurate of the formula (I)

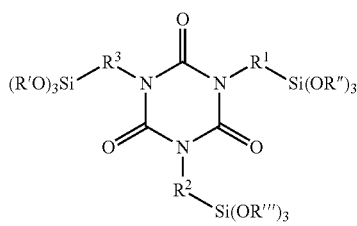

(formula I)

The examples adduced hereinafter describe the present invention by way of example, without any intention that the invention, the scope of application of which is apparent from the entirety of the description and the claims, be restricted to the embodiments specified in the examples.

EXAMPLES

Unless stated otherwise, the percentages stated in the examples are based on weight.
Input Materials:
Bona Traffic HD: Binder component of the two-component polyurethane dispersion (Bona Vertriebsgesellschaft mbH Deutschland)
Bona Traffic Hardener: Hydrophilic, aliphatic polyisocyanate, as hardener component for Bona Traffic HD (Bona Vertriebsgesellschaft mbH Deutschland)
Dynasylan® VPS 7161: Isocyanatopropyltrimethoxysilane trimer (Evonik Resource Efficiency GmbH)
Dynasylan® Hydrosil 2926: Reactive organofunctional siloxane oligomer in water (Evonik Resource Efficiency GmbH)
Dynasylan® Sivo 160: Water-based, amine-modified silicone (Evonik Resource Efficiency GmbH)
Polyglykol M500 PU: Linear, monohydroxy-functional polyethylene glycol monomethyl ether (Clariant International Ltd.)
Vestanat® EP Cat 11 H: Tetraethylammonium benzoate in water (Evonik Resource Efficiency GmbH)
1. Preparation of Hydrophilic Crosslinkers Example 1

Hydrophilic Crosslinker U1
620.24 g of Dynasylan VPS 7161 and 179.76 g of Polyglykol M500 PU were charged to a three-necked flask with distillation bridge and this initial charge was blanketed with nitrogen. The contents of the flask were heated to 150° C. with stirring and the temperature was maintained for 10 hours under a gentle stream of nitrogen. Following distillative removal of 9.6 g of methanol, corresponding to a conversion of 81%, the mixture was cooled and the hydrophilic crosslinker U1 was obtained as a yellow liquid with a viscosity of 216 mPas (at 23° C.).

Example 2

Hydrophilic crosslinker U2
a) Synthesis of Emulsifier B for the Hydrophilic Crosslinker U2
A three-litre autoclave was charged with 800 g of Polyglykol M500 PU and 8.4 g of potassium methoxide, under nitrogen, and this initial charge was heated to 115° C. with stirring. The reactor was evacuated down to an internal pressure of 30 mbar, in order to effect distillative removal of any volatile ingredients present. At 115° C., 474.7 g of dodecene oxide were metered in over the course of 15 minutes. Within the subsequent reaction time of 2.5 hours, the internal temperature was raised to 125° C. This was followed by the devolatilization stage, during which volatile fractions such as residual alkylene oxide were removed by distillation under reduced pressure. The polyether, which was still alkaline, was cooled to 95° C. and deodorized under a reduced pressure of approximately 20 mbar. This was followed by neutralization with aqueous phosphoric acid. Subsequently, at 115° C. and under reduced pressure, water was removed by distillation. After cooling to <80° C., the end product was discharged from the reactor via a filter.
The resulting emulsifier had an OH number of 74 mg KOH/g and an average molar mass of 760 g/mol. Free epoxide groups were not detectable in the end product. The acid number was 0.1 mg KOH/g.
b) Synthesis of the Hydrophilic Crosslinker U2
275.04 g of Dynasylan VPS 7161 and 124.96 g of the hydrophilizing agent from b) were charged to a three-necked flask with distillation bridge and this initial charge was blanketed with nitrogen. The contents of the flask were heated to 150° C. with stirring and the temperature was maintained for 12 hours under a gentle stream of nitrogen. Following distillative removal of 4.9 g of methanol, corresponding to a conversion of 93%, the mixture was cooled and the hydrophilic crosslinker U2 was obtained as a clear, light brown liquid having a viscosity of 333 mPas (at 23° C.).

Example 3

Hydrophilic Crosslinker U3 (Si-UM-water 21)
At room temperature, 25.0 g of hydrophilic crosslinker U1 were homogenized with 16.1 g of Dynasylan VPS 7161, with stirring. The hydrophilic crosslinker U3 obtained after mixing was a clear, light yellow liquid and was used subsequently for the stability test (see below).

Example 4 (Non-Inventive)

Mixture of Dynasylan VPS 7161 and Polyglykol M500 PU
At room temperature, 25.5 g of Dynasylan VPS 7161 were homogenized with 4.5 g of Polyglykol M500 PU, with stirring. The resulting mixture was used subsequently for the stability test (see below).

Example 5 (Non-Inventive)

Mixture of Dynasylan UPS 7161 and Polyglykol M350 PU
At room temperature, 25.5 g of Dynasylan VPS 7161 were homogenized with 4.5 g of Polyglykol M350, with stirring. The resulting mixture was used subsequently for the stability test (see below).

Example 6 (Non-Inventive)

Mixture of Dynasylan UPS 7161 and Emulsifier B (see Example 2)
At room temperature, 24 g of Dynasylan VPS 7161 were homogenized with 6 g of emulsifier B, with stirring. The resulting mixture was used subsequently for the stability test (see below).
2. Stirrability into Water and Service Life
The products produced in examples 1 -6 and also the commercial products Dynasylan VPS 7161 and Bona Traffic Hardener were stirred at 30 wt % into water in a 250 ml wide-necked flask using a high-speed stirrer (2 min at 1000 rpm and additionally 1 min at 1500 rpm) and were left to stand at room temperature.

To determine the service life, the samples containing examples 1-6 or Dynasylan VPS 7161 were visually inspected and regularly tested for surface gelling with a wooden spatula. A measurement was made of the time taken for the sample to gel, thus indicating the end of the service life in water. The gelling was a sign of a strong $Si(OR)_3$/water reaction. The sample was classified as "gelled" when it was present in the form of a homogeneous gel body, in other words an elastic solid/mass of firm consistency.

The Bona Traffic Hardener product was a hydrophilic polyisocyanate. The service life in water was defined here via the formation of foam, which indicates the reaction between water and the isocyanate function with accompanying formation of carbon dioxide.

TABLE 1

Stirrability into water and service lives

| HPIC | Appearance after stirred incorporation. | Service life in water |
|---|---|---|
| Dynasylan VPS 7161 | Poor; immediate phase separation | n.d. |
| Traffic Hardener | Good; fine dispersion | >3 h |
| Example 1 (hydrophilic crosslinker U1) | Good; fine dispersion | 30 min |
| Example 2 (hydrophilic crosslinker U2) | Good; fine dispersion | >3 h |
| Example 3 (hydrophilic crosslinker U3) | Good; fine dispersion | 16 min |
| Example 4 (comparative) | Poor; immediate phase separation | n.d.* |
| Example 5 (comparative) | Poor; immediate phase separation | n.d.* |
| Example 6 (comparative) | Poor; immediate phase separation | n.d.* |
| Dynasylan Hydrosil 2926 (comparative) | Clear solution | >3 h |
| Dynasylan Sivo 160 (comparative) | Clear solution | >3 h |

*n.d. = not determined, since there was no dispersion.

The hydrophilic crosslinkers U1, U2 and U3 of the invention can be incorporated equally well into water by dispersion as the commercially available hydrophilic polyisocyanate Traffic Hardener (see table 1).

The non-inventive examples 4-6 show that a stable dispersion was unattainable if the hydrophilizing agent was present only as a physical mixture alongside the alkoxysilane-containing isocyanurate A), here in the form of Dynasylan VPS7161. Surprisingly, only a stable dispersion was obtained if the hydrophilizing agent had been built on chemically, by means of transesterification, onto the alkoxysilane-containing isocyanurate A), here in the form of Dynasylan VPS7161, and was therefore present as a hydrophilic crosslinker U of the invention.

The hydrophilic crosslinker U2 of the invention exhibited a stability of >3 h in water and therefore had the same stability in water as the commercially available hydrophilic polyisocyanates (example: Bona Traffic Hardener).

Surprisingly, the hydrophilic crosslinker U3, which had a lower fraction of hydrophilizing agent, possesses a higher reactivity than the hydrophilic crosslinker U1.

3. Production of an RT-Curing Clearcoat Using Hydrophilic Crosslinker

For the formulation of the inventive RT-curing clearcoats and of the comparative examples, the components of the compositions represented in Table 2 were employed. For formulations I-VI, the crosslinkers, irrespective of their solids content, were used in a weight ratio of Bona Traffic HD to crosslinker of 9:1 based on as-supplied form. In the inventive formulation VII, the amount of the hydrophilic crosslinker U2 of the invention (solids content 100%) was reduced in order to create better comparability with the Dynasylan Hydrosil 2926, which had a solids content only of 30%.

To produce the formulations, the binder component (here: Bona Traffic HD) was introduced into a bottle, the hydrophilic crosslinker was added, and the mixture was stirred intensively with a wooden spatula for approximately 30 seconds. A homogeneous dispersion was formed. This dispersion was filtered through an 80μ filter and then knife-coated with a film thickness of 15-35 μm onto steel panels (Gardobond GB26S 60 OC) using a 120 μm wire-wound doctor. This coated panel was then left to stand and then subjected to analytical testing at room temperature. Formulation VI developed a high viscosity even during homogenization, and therefore could not be applied.

From Table 3 it is evident that the film-forming properties of the coatings III and IV, containing the hydrophilic crosslinkers U1 and U2 of the invention, showed better chemical resistances (MEK test) than the Bona Traffic Hardener, a hydrophilic polyisocyanate. The inventive coating VII as well exhibited better chemical resistance than the coating V with the Dynasylan Hydrosil 2926. The hydrophilic crosslinker U2 of the invention, moreover, exhibited a pot life of 4 h in the two-component system, and therefore had a stability matching that of the commercially available hydrophilic polyisocyanates, in the present case Bona Traffic Hardener.

TABLE 2

Composition of the inventive RT-curing clearcoats and comparative example, figures in weight fractions

| Item | | I | II | III (inventive) | IV (inventive) | V | VI* | VII (inventive) |
|---|---|---|---|---|---|---|---|---|
| 1 | Bona Traffic HD (binder component) | 10 | 9 | 9 | 9 | 9 | 9 | 9 |
| 2 | Bona Traffic Hardener | | 1 | | | | | |
| 3 | Example 1 (hydrophilic crosslinker U1) | | | 1 | | | | |
| 4 | Example 2 (hydrophilic crosslinker U2) | | | | 1 | | | 0.3 |
| 5 | Dynasylan Hydrosil 2926 | | | | | 1 | | |
| 6 | Dynasylan Sivo 160 | | | | | | 1 | |

TABLE 2-continued

Composition of the inventive RT-curing clearcoats and comparative example, figures in weight fractions

| Item | | I | II | III (inventive) | IV (inventive) | V | VI* | VII (inventive) |
|---|---|---|---|---|---|---|---|---|
| 7 | Vestanat Cat 11 H | | | 0.05 | 0.05 | 0.05 | 0.05 | 0.05 |
| 8 | Water | | | 0.8 | 0.8 | | 8 | |

*VI Coating formulation became high viscous despite dilution with water, and could not be applied.

TABLE 3

Coating properties of the compositions I-IV after curing at 23° C. (7 days)

| Composition | I | II | III (inventive) | IV (inventive) | V | VII (inventive) |
|---|---|---|---|---|---|---|
| Erichsen cupping [mm] (EN ISO 1520) | 8.0 | 8.0 | 9.0 | 8.0 | 7.0 | 8.0 |
| Ball impact [inch lbs] (DIN-EN-ISO 6272-1) | >80 | >80 | >80 | >80 | >80 | >80 |
| MEK test [ASTM D 4752] (Double rubs, 1 kg applied weight) | 10 | 80 | >150 | >150 | 50 | >150 |
| Pot life of the two-component system | — | 4 h | 1 h | 4 h | >4 h | >4 h |

The pot life of the two-component system was the time within which the formulation from Table 2, after having been produced, still passes the specified MEK test.

European patent application 17172009.7 filed May 19, 2017, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An alkoxysilane-containing isocyanurate of formula (II)

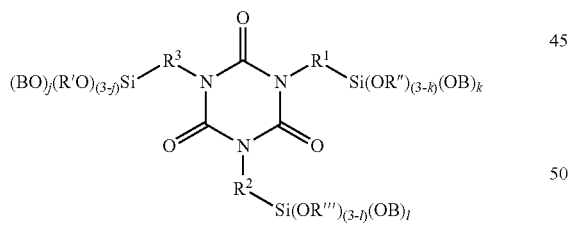

(formula II)

wherein
$R^1$, $R^2$ and $R^3$ are, in each case independently of one another, a linear, a branched, or a cyclic $C_1$-$C_8$ alkylene radical,
R', R" and R''' are, in each case independently of one another, a linear, a branched, or a cyclic $C_1$-$C_8$ alkyl radical,
j, k, l, are each independently of one another, 0, 1, 2 or 3, $1 \leq j+k+l \leq 7$, and
radical —OB is a polyalkylene oxide polyether alkoxy radical, or
radical —OB has formula —O{(X)-(y)$_a$-(Z)}, wherein
radical X derives from a hydroxypolyethylene glycol ether of empirical formula HO(CH$_2$CH$_2$O)$_n$T$^1$, wherein n=2-100, wherein T$^1$=H or $C_1$-$C_6$ alkyl, or from a hydroalkylcarboxylic acid, or from a hydroxypolyethersulfonic acid, a is 0 or 1, radical y, if present, derives from a di- or polyisocyanate, from a di- or polycarboxylic acid derivative, from a di- or polyepoxide, from a mono- or polyalkoxysilane, from an epoxyisocyanate, from an epoxyalkoxysilane or from an isocyanatosilane, and radical Z derives from a hydroxy-terminated polyether of formula TO(CTHCH$_2$O)$_n$(CH$_2$CH$_2$O)$_p$T', wherein T=—(CH$_2$)$_m$CH$_3$, n and m independently of one another=0-20, p=0-5 wherein n is greater than or equal to 4 times p, and T'=H or $C_1$-$C_{18}$ alkyl, or from one or more than one hydroxyhydrocarbon having 1-18 carbon atoms, which is optionally branched and/or optionally contains rings and/or heteroatom(s), or from an alkylene oxide having at least four carbon atoms which is optionally branched and/or optionally contains rings.

2. The isocyanurate according to claim 1, wherein $R^1=R^2=R^3=$—CH$_2$—, —CH$_2$CH$_2$—, —CH$_2$CH$_2$CH$_2$— or —CH$_2$CH$_2$CH$_2$CH$_2$—, and R', R" and R''' are identical and selected from the group consisting of —CH$_3$, —CH2CH$_3$, and —CH(CH$_3$)CH$_3$.

3. The isocyanurate according to claim 2, wherein $R^1=R^2=R^3=$—CH$_2$CH$_3$CH$_2$— and R', R" and R''' are identical and selected from the group consisting of —CH$_3$ and —CH$_2$CH$_3$.

4. The isocyanurate according to claim 1, wherein
the polyalkylene oxide polyether alkoxy radical is a polyethylene glycol monomethyl ether alkoxy radical having on average 5 to 30 ethylene oxide units.

5. The isocyanurate according to claim 1, wherein radical X derives
from a hydroxypolyalkylene glycol ether of empirical formula $HO(CH_2CH_2O)_nT^1$ wherein n=2-100, where $T^1$=H or $C_1$-$C_6$ alkyl, and
radical Z has formula -G-D-H, wherein
G is a structural element of formula (III)

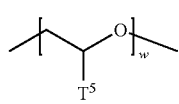
(III)

wherein $T^5$ independently at each occurrence is a saturated, unsaturated, branched or unbranched, substituted or unsubstituted hydrocarbon radical having at least two carbon atoms,
and w is greater than or equal to one;
D is an oxyethylene radical or oxypropylene radical of formula $—(CH_2CHT^6O)_v$ wherein v is greater than or equal to 0, and $T^6$=—H or —$CH_3$; and
H=hydrogen.

6. A process for preparing the isocyanurate according to claim 1, the process comprising:
reacting at least one alkoxysilane-containing isocyanurate of formula (I)

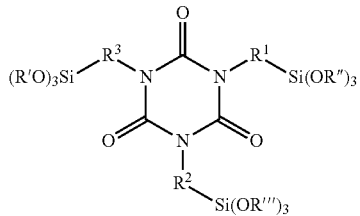
(formula I)

with at least one hydrophilizing agent of formula BOH, which has at least one OH group,
wherein
$R^1$, $R^2$ and $R^3$ are, in each case independently of one another, a linear, a branched, or a cyclic $C_1$-$C_8$ alkylene radical,
R', R" and R'" are, in each case independently of one another, a linear, a branched, or a cyclic $C_1$-$C_8$ alkyl radical, and
B is a hydrophilic radical.

7. The process according to claim 6, wherein
the alkoxysilane-containing isocyanurate of formula (I) and the hydrophilizing agent BOH are present in a (I)/BOH molar ratio of from 15:1 to 1:7.

8. A coating or plastics formulation, a crosslinker, an emulsifier, an admixture for mineral building materials and/or an adjuvant for aqueous polyurethane dispersions, comprising:
the isocyanurate according to claim 1.

9. A coating or plastic formulation, comprising:
the isocyanurate according to claim 1.

10. A coating or plastic formulation according to claim 9, further comprising:
at least one isocyanurate of formula (I)

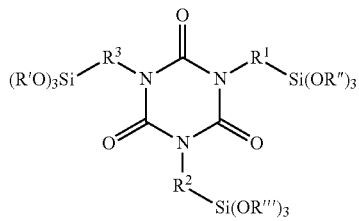
(formula I)

wherein
$R^1$, $R^2$ and $R^3$ are, in each case independently of one another, a linear, a branched, or a cyclic $C_1$-$C_8$ alkylene radical, and
R', R" and R'" are, in each case independently of one another, a linear, a branched, or cyclic $C_1$-$C_8$ alkyl radical.

* * * * *